US011578021B1

(12) United States Patent
Mohan et al.

(10) Patent No.: US 11,578,021 B1
(45) Date of Patent: Feb. 14, 2023

(54) ROOM-TEMPERATURE, CATALYST-FREE ALKANE CHLORINATION

(71) Applicant: THE BOARD OF TRUSTEES OF THE UNIVERSITY OF ILLINOIS, Urbana, IL (US)

(72) Inventors: Varun Mohan, Santa Clara, CA (US); Prashant Jain, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 17/851,819

(22) Filed: Jun. 28, 2022

Related U.S. Application Data

(60) Provisional application No. 63/218,609, filed on Jul. 6, 2021.

(51) Int. Cl.
C07C 17/10 (2006.01)
C07C 17/06 (2006.01)
C07C 17/093 (2006.01)

(52) U.S. Cl.
CPC ............ C07C 17/06 (2013.01); C07C 17/093 (2013.01); C07C 17/10 (2013.01)

(58) Field of Classification Search
CPC ........ C07C 17/06; C07C 17/093; C07C 17/10
See application file for complete search history.

(56) References Cited

FOREIGN PATENT DOCUMENTS

WO   WO-2020178075 A1 * 9/2020

OTHER PUBLICATIONS

Bilke, M. et al. "Methane to Chloromethane by Mechanochemical Activation: A Selective Radical Pathway" J. Am. Chem. Soc. 2019, 141, 11212-11218 (Year: 2019).*
Huo, S. et al. "Methane Activation with N-Haloimides" Ind. Eng. Chem. Res. 2020, 59, 22690-22695 and Supporting information S1-S29 (Year: 2020).*
Olah, George A., et al., "Selective Monohalogenation of Methane over Supported Acid or Platinum Metal Catalysts and Hydrolysis of Methyl Halides over γ-Alumina-Supported Metal Oxide/Hydroxide Catalysts. A Feasible Path for the Oxidative Conversion of Methane into Methyl Alcohol/Himethyl Ether", American Chemical Society, 9 pages, 1985.
Bamji, Zubin, Global Gas Flaring Tracker Report, Global Gas Flaring Reduction Partnership (GGFR), The World Bank, Jul. 2020, 6 pages.
Global Gas Flaring Tracker Report, Understanding Poverty, The World Bank Group, https://www.worldbank.org/en/topic/extractiveindustries/publication/global-gas-flaring-tracker-report, Apr. 28, 2021, 5 pages.

Wan, Zhijian, et al., "Effect of reaction conditions on methanol to gasoline conversion over nanocrystal ZSM-5 zeolite", Catalysis Today, 314, pp. 107-113, Jan. 20, 2018.
Wahman, David G., "Chlorinated Cyanurates: Review of Water Chemistry and Associated Drinking Water Implications", Journal Awwa, Sep. 2018, 110:9, pp. E1-E15.
Zuckerman, J.J., "The Direct Synthesis of Organosilicon Compounds", Adv. Inorg. Chem. Radiochem, 1964, pp. 383-432.
Zichittella, Guido, et al., "Olefins from Natural Gas by Oxychlorination", Angew. Chem. Int Ed., 56, 2017, pp. 13670-13674.
Zhou, Linan, et al., "Light-driven methane dry reforming with single atomic site antenna-reactor plasmonic photocatalysts", Nature Energy, vol. 5, 2020, pp. 61-70.
Chattaway, F.D., et al., "The Constitution of Hydrocyanic, Cyanic, and Cyanuric Acids", 1902, pp. 191-203.
Batamack, Patrice T.D., et al., "One-Pot Conversion of Methane to Light Olefins or Higher Hydrocarbons through H-SAPO-34-Catalyzed in Situ Halogenation", J. Am. Chem. Soc., 139, 2017, pp. 18078-18083.
Bilke, Marius, et al., "Methane to Chloromethane by Mechanochemical Activation: A Selective Radical Pathway", J. Am. Chem. Soc., 141, 2019, pp. 11212-11218.
Brady, A.P., et al., "Equilibria in Solutions of Cyanuric Acid and its Chlorinated Derivatives", vol. 85, 1963, pp. 3101-3104.
Horvath, Istvan T., et al., "Low-Temperature Methane Chlorination with Aqueous Platinum Chlorides in the Presence of Chlorine", Organometallics, 12, 1993, pp. 8-10.
Huang, Jincan, et al., "Enhanced Light Olefin Production in Chloromethane Coupling over Mg/Ca Modified Durable HZSM-5 Catalyst", Ind. Eng. Chem. Res., 58, 2019, pp. 5131-5139.
Karlsson, Rasmus K.B., et al., "Selectivity between Oxygen and Chlorine Evolution in the Chlor-Alkali and Chlorate Processes", Chem. Rev., 116, 2016, pp. 2982-3028.
Diaz-Urrutia, Christian, et al., "Activation of methane: A selective industrial route to methanesulfonic acid", Science 363, 2019, pp. 1326-1329.
Gunsalus, Niles J., et al., "Homogeneous Functionalization of Methane", Chem. Rev., 117, 2017, pp. 8521-8573.
Schwach, Pierre, et al., "Direct Conversion of Methane to Value-Added Chemicals over Heterogeneous Catalysts: Challenges and Prospects", Chem. Rev., 117, 2017, pp. 8497-8520.
Paunović, Vladimir, et al., "Selective Methane Functionalization via Oxyhalogenation over Supported Noble Metal Nanoparticles", ACS Catal., 9, 2019, pp. 1710-1725.
Podkolzin, Simon G., et al., "Methyl Chloride Production from Methane over Lanthanum-Based Catalysts", J. Am. Chem. Soc., 129, 2007, pp. 2569-2576.

(Continued)

Primary Examiner — Medhanit W Bahta
(74) Attorney, Agent, or Firm — Dilworth IP, LLC

(57) ABSTRACT

A process for alkane chlorination comprising: (a) providing an aqueous solution comprising dissolved alkanes selected from methane, ethane or combinations thereof; (b) providing an 0.005 to 0.050 M aqueous solution of trichloroisocyanuric acid, wherein the trichloroisocyanuric acid in solution forms cyanuric acid and hypochlorous acid; and (c) contacting the aqueous solution comprising dissolved alkanes with the aqueous solution of trichloroisocyanuric acid, wherein a liquid phase reaction between the dissolved alkanes and the hypochlorous acid forms a gaseous product stream comprising at least one of chloromethane and chloroethane.

29 Claims, 12 Drawing Sheets

(56) References Cited

OTHER PUBLICATIONS

Schüth, Ferdi, "Making more from methane", Science, vol. 363, No. 6433, 2019, 3 pages.
O'Brien, J.E., et al., "Chapter 14: Equilibria in Aqueous Solutions of Chlorinated Isocyanurate", Ann Arbor Science Publishers, Inc., 1974, pp. 333-358.
Ogura, Kotaro, et al., "Direct conversion of methane to methanol, chloromethane and dichloromethane at room temperature", Nature, vol. 319, 1986.
Olah, George A., "After oil and gas: methanol economy", Catalysis Letters, vol. 93, Nos. 1-2, 2004.
Lin, Ronghe, et al., "Halogen-Mediated Conversion of Hydrocarbons to Commodities", Chem. Rev., 117, 2017, 4182-4247.
Litvinenko, S.L., et al., "DFT Analysis of the Mechanism for the Gas-Phase Chlorination of Methane in the HOCl-H2O System", Theoretical and Experimental Chemistry, vol. 48, No. 4, Sep. 2012 (Russian Original vol. 48, No. 4, Jul.-Aug. 2012).
Martinez-Vargas, Daniela Xulú, et al., "Recent Advances in Bifunctional Catalysts for the Fischer-Tropsch Process: One-Stage Production of Liquid Hydrocarbons from Syngas", Ind. Eng. Chem. Res., 58, 2019, pp. 15872-15901.
Laudadio, Gabriele, et al., "C(sp3)-H functionalizations of light hydrocarbons using decatungstate photocatalysis in flow", Science, 369, 2020, pp. 92-96.
Leow, Wan Ru, et al., "Chloride-mediated selective electrosynthesis of ethylene and propylene oxides at high current density", Science, 368, 2020, pp. 1228-1233,.

* cited by examiner

ROOM-TEMPERATURE, CATALYST-FREE ALKANE CHLORINATION

FIELD OF THE INVENTION

The present invention relates to a process for upgrading alkanes. More particularly, the present invention relates to a low temperature process for chlorinating methane or ethane without a catalyst.

BACKGROUND OF THE INVENTION

Methane ($CH_4$), the principal component of natural gas, is an abundant source of carbon. Large reserves of natural gas remain untapped, however, due to their prevalence in isolated regions of the world. Costly compression and transportation would be required for their utilization. Additionally, vast amounts are flared every year during oil drilling operations, thereby injecting an estimated 400 million tons per year of $CO_2$ into the earth's atmosphere. Methane is also produced as light end products in chemical plants and refineries. While sometimes the gas can be captured and productively utilized as a part of a gas for fueling boilers and furnaces, it is often simply flared. However, the petrochemical industry is just one source of methane. Other sources include landfills, wastewater treatment plants, and aerobic and anaerobic digesters.

Thus, conversion of methane in situ to higher hydrocarbons or value-added products, such as olefins and polymers, is attractive not only from the standpoint of conservation of natural resources and pollution prevention, but also for expanding economically viable reserves of an important feedstock. Halogenation of methane is an effective means for mediating its activation and lowering the activation barrier for upgradation reactions. Monochlorination of methane replaces the unreactive C—H bond with a C—Cl bond, which allows easier oxidation or coupling reactions. Furthermore, chloromethane itself has use as a methylating agent. It can be converted by hydrolysis with steam to methanol, which in turn is an industrial solvent, a liquid fuel for transportation and direct-methanol fuel cells, and a raw material for the production of chemicals. Chloromethane may also be directly subject to coupling reactions over zeolite-based catalysts to form olefins and feedstocks for widely used organosilicon compounds. Commonly used methods for methane chlorination usually require elevated temperatures and expensive reagents or catalysts. Efforts to develop less demanding processes for methane chlorination have been ongoing. Some laboratory procedures have accomplished methane chlorination under relatively mild conditions; however, additional sources of energy such as ultraviolet (UV) light or electrochemical input had to be employed. Recently, in Methane to chloromethane by mechanochemical activation: A selective radical pathway, J. Am. Chem. Soc. 141, 11212-11218 (2019), Bilke et al., trichloroisocyanuric acid (TCCA) and a mechanochemically activated solid-gas process were used to chlorinate methane at moderate (~100° C.) temperatures. In this process, mechanical impact on solid Lewis-acid catalysts is thought to assist in the cleavage of the N—Cl bonds of trichloroisocyanuric acid, yielding $N^{\cdot}$ and $Cl^{\cdot}$, and leading further to the free-radical-mediated chlorination of methane. Nevertheless, a continuing need exists for improved methods of methane chlorination. Indeed, a process to similarly upgrade ethane is also needed. This specification describes a process for the chlorination of methane or ethane that takes place near room temperature without a catalyst or external energy input.

SUMMARY OF THE INVENTION

The subject matter of the present disclosure relates to a process for producing chloromethane or chloroethane at room temperature without catalysts.

In one embodiment, the invention relates to a process for alkane chlorination comprising: (a) providing an aqueous solution comprising dissolved alkanes selected from methane, ethane or combinations thereof; (b) providing an 0.005 to 0.050 M aqueous solution of trichloroisocyanuric acid, wherein the trichloroisocyanuric acid in solution forms cyanuric acid and hypochlorous acid; and (c) contacting the aqueous solution comprising dissolved alkanes with the aqueous solution of trichloroisocyanuric acid, wherein a liquid phase reaction between the dissolved alkanes and the hypochlorous acid forms a gaseous product stream comprising at least one of chloromethane and chloroethane.

In another embodiment, the invention relates to a process for the production of chloromethane or chloroethane comprising: (a) providing an aqueous solution comprising dissolved alkanes selected from methane, ethane or combinations thereof; (b) providing a mixture of water and solid trichloroisocyanuric acid, wherein the solid trichloroisocyanuric acid dissolves in the water to form cyanuric acid and hypochlorous acid; and (c) contacting the aqueous solution containing dissolved alkanes with the aqueous solution containing trichloroisocyanuric acid, wherein a liquid phase reaction between the dissolved alkanes and the hypochlorous acid forms a gaseous product stream comprising at least one of chloromethane and chloroethane.

In still another embodiment, the invention relates to a process for the production of chloromethane or chloroethane comprising: (a) providing an aqueous solution comprising dissolved alkanes selected from methane, ethane or combinations thereof; and (b) adding solid trichloroisocyanuric acid to the aqueous solution comprising dissolved alkanes, wherein the solid trichloroisocyanuric acid dissolves to form cyanuric acid and hypochlorous acid, and a liquid phase reaction between the dissolved alkanes and hypochlorous acid forms a gaseous product stream comprising at least one of chloromethane and chloroethane.

In another embodiment, the invention relates to a process comprising: (a) adding an aqueous solution comprising dissolved alkanes selected from methane, ethane or combinations thereof to a reactor comprising a liquid phase stream and a bulk gas phase stream above the liquid phase; and (b) adding solid trichloroisocyanuric acid to the aqueous solution comprising dissolved alkanes, wherein the solid trichloroisocyanuric acid dissolves to form cyanuric acid and hypochlorous acid, and a liquid phase reaction between the dissolved alkanes and hypochlorous acid forms a gaseous product stream comprising a chlorinated alkane product comprising at least one of chloromethane and chloroethane that moves to the bulk gas phase stream of the reactor, wherein the bulk gas phase stream comprises the chlorinated alkane products and at least one of methane and ethane.

BRIEF DESCRIPTION OF THE DRAWINGS

The subject matter of the present disclosure will be more fully understood from the following detailed description, taken in connection with the accompanying drawings, in which.

DETAILED DESCRIPTION OF THE INVENTION

Figure 1A:
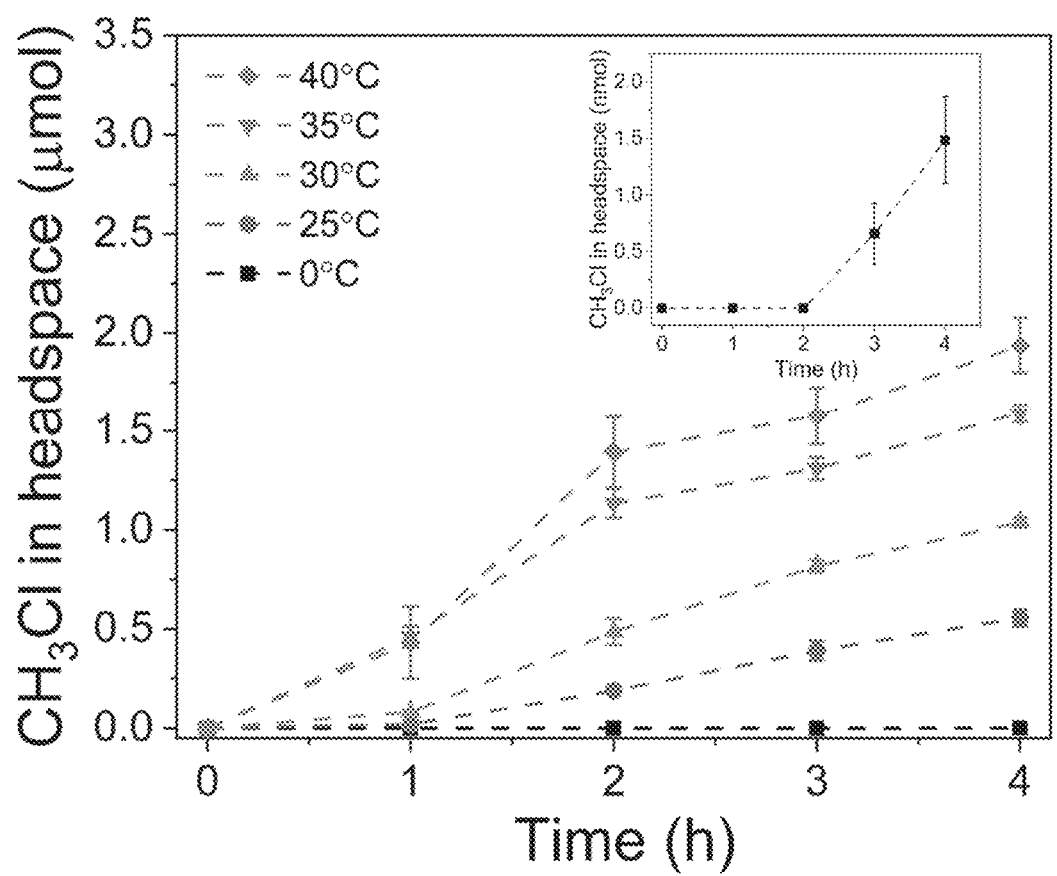
FIG. 1A illustrates conversion-time plots for the production of chloromethane in 4 hr. reactions at a fixed amount of trichloroisocyanuric acid and different reaction temperatures. The inset shows a magnified conversion-time plot for the case of 0° C.

Described in this specification is a simple process for the chlorination of the alkane products methane and/or ethane at room temperature under mild conditions, using minimal reagents and no catalysts or external sources of energy. The reaction is carried out in an aqueous medium with trichloroisocyanuric acid (TCCA) as a chlorinating agent. The dissolution of trichloroisocyanuric acid in water leads to the sustained and buffered release of hypochlorous acid, which triggers the chlorination of methane or ethane by a free-radical mechanism. In this specification, unless otherwise stated, references to the chlorination of methane also apply to the chlorination of ethane, and vice versa.

The process utilizes the chlorinating agent, trichloroisocyanuric acid, dissolved in an aqueous medium saturated with methane and/or ethane. No other sources of activation, high temperature, or catalysts are required. Trichloroisocyanuric acid is commonly used as a bleaching and water disinfection agent in swimming pools and other water sources because it is a stable and sustained source of free chlorine when added to water. At low to moderate pH, this free chlorine is in the form of hypochlorous acid (HOCl). Trichloroisocyanuric acid gradually dissolves in water and dissociates to form cyanuric (isocyanuric) acid (CA) and hypochlorous acid (HOCl) in the aqueous medium, as shown in reaction (1). In the reaction scheme of the present process, hypochlorous acid then acts to chlorinate dissolved methane to form chloromethane, as shown in reaction (2).

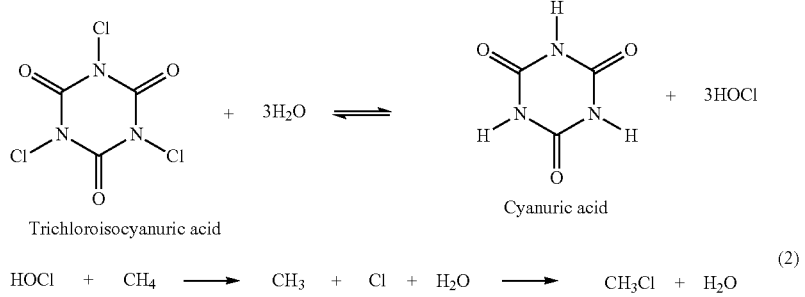

The chlorination mechanism is free-radical mediated. The slow, sustained release of hypochlorous acid into the aqueous medium by the gradual dissolution and dissociation of trichloroisocyanuric acid over the course of the reaction allows for controlled chlorination.

The formation of chloromethane and its removal into the vapor phase also acts as a chlorine sink, shifting the trichloroisocyanuric acid dissociation equilibrium:

$$TCCA + H_2O \rightleftharpoons CA + HOCl \qquad (3)$$

toward the right and promoting the release of additional hypochlorous acid. This simple reaction scheme eliminates the need for catalysts or expensive reagents and can take place at room temperature. This system not only provides a source for hypochlorous acid, but also facilitates stabilization of the hypochlorous acid by the cyanuric acid, CA, to prevent undesirable rapid decomposition. Thus, a source of hypochlorous acid alone will not be sufficient to obtain appreciable conversion. The hypochlorous acid needs to be stabilized against decomposition in the aqueous reaction medium. Cyanuric acid, the organic backbone that remains in water after the release of hypochlorous acid from trichloroisocyanuric acid, functions as such a stabilizer.

The process for alkane chlorination as described in the present specification involves forming an aqueous solution with dissolved methane or ethane. The methane utilized in such a process can originate from sources such as chemical plants, refineries, wastewater treatment plants, landfills, aerobic digesters or anaerobic digesters, as well as from more conventional natural gas deposits.

One skilled in the art would recognize that such a process can be conducted in conventional equipment suitable to the materials, pressures and temperatures involved, where methane or ethane is contacted with water via conventional means, for example by bubbling methane through the water or by using a diffuser. The process can be either continuous or batch. The vessel used to dissolve the alkane can also be a reactor, i.e., the vessel can also be the reactor where the alkane is chlorinated. Such reactor vessels can include any conventional equipment suitable for the reactor conditions (temperature, pressure), and reactant medium, e.g., a tubular reactor or a continuous stirred tank reactor. Methane or ethane will be dissolved in the aqueous solution to form a concentration of dissolved methane or ethane, preferably, from 1.1 mM to 1.3 mM. The upper limit of the methane concentration is the saturation point of methane in water at that temperature and pressure.

Methane or ethane present in a vapor space above the aqueous solution can also be recirculated back through the aqueous solution using a compressor. Water used to dissolve the methane or ethane preferably has a total organic carbon (TOC) level of less than 25 ppm; preferably, a chlorides level of 250 mg/l; preferably, an electrical conductivity of less than 2500 $\mu S\ cm^{-1}$ at 20° C.; preferably, a pH of 6.5 to 8.5; preferably, a total dissolved solid concentration of less than 500 mg/l, and preferably is free of undissolved solids. In the case of methane, the temperature at which methane is preferably introduced into the aqueous solution can be from 0 to 96° C., preferably, 25 to 40° C. The pressure at which methane is preferably introduced and dissolved is ~1 atm or higher. Higher pressures would allow higher saturation concentrations of dissolved methane in the aqueous medium.

The solid trichloroisocyanuric acid used is preferably in the form of a pellet, powder or granule. When present as a pellet, preferably, the diameter of the pellet is from 1.0 to 5.0 mm. Preferably, the trichloroisocyanuric acid is >89.5% analytical specification as determined by a silver nitrate titration assay.

The trichloroisocyanuric acid is added to the aqueous solution in an amount to provide a 0.005 to 0.050 M solution, preferably, 0.01 to 0.04 M. In solution, i.e., in the reaction solution, the trichloroisocyanuric acid dissociates to form cyanuric acid and hypochlorous acid. The dissociation can be enhanced by mixing with conventional mixing equipment. One skilled in the art would understand that unless supplemented, trichloroisocyanuric acid will be consumed in the reaction. However, it can be regenerated from the cyanuric acid generated in the aqueous medium by treating it with chlorine gas in the presence of sodium hydroxide.

The principle products of the reaction are chloromethane, chloroethane or combinations thereof, with minor products being oxalyl chloride, $(COCl)_2$, methyl nitrate $(CH_3NO_3)$ and overchlorinated compounds.

While the chlorination process may proceed beyond monochlorination to form overchlorinated products such as di- or trichloromethane, these products are minor relative to monochlorinated product.

Because the vapor space above the reaction solution likely contains large amounts of alkane, the reaction product that escapes into the vapor phase mixes with alkane in the vapor space to form a bulk mixed methane/ethane and chloromethane/chloroethane stream. The product of the reaction can also be stored or treated directly to separate chloromethane from other components in the gas stream.

The saturated alkane solution and trichloroisocyanuric acid may be contacted in a number of ways. First, the dissolved alkane solution can be separately prepared, and contacted with an aqueous solution of trichloroisocyanuric acid. Second, a separately prepared dissolved alkane solution can be contacted with an aqueous solution containing solid trichloroisocyanuric acid. Finally, solid trichloroisocyanuric acid can be added to the aqueous solution of dissolved alkane. The reaction between the dissolved alkane and hypochlorous acid takes place in the liquid phase to form chloromethane or chloroethane gas. The temperature of the liquid phase, i.e., the reaction solution, in which the reaction takes place, preferably ranges from 0° C. to 96° C., more preferably, 0° C. to 40 ° C., even more preferably, 20° C. to 40° C. Preferably, the pH of the liquid phase is 2.0 to 3.5, more preferably, 2.5 to 3.0. The kinetics of the reaction are affected by the temperature of the reaction solution and the initial concentration of trichloroisocyanuric acid. For example, in the case of methane, ~1 µmol of chloromethane is produced in the headspace in 4 hr. for the reaction conducted at 30° C. with 10 mg (0.015 M when fully dissolved) of trichloroisocyanuric acid. For the reaction conducted with 30 mg (0.043 M when fully dissolved) of trichloroisocyanuric acid at the same temperature, ~4 µmol of chloromethane is produced in the headspace in 4 hr.

The following examples further detail and explain the performance of the inventive process to produce chloromethane or chloroethane using trichloroisocyanuric acid. Those skilled in the art will recognize many variations that are within the spirit of the invention and scope of the claims.

Experimental Methods

Preparation of reaction mixtures:

All reagents were purchased from Sigma-Aldrich and used as received, unless specified otherwise. In a typical procedure, a specified amount of trichloroisocyanuric acid (TCCA, >89.5%) in pellet form was mixed with 3 mL of deionized (DI) water in a 10 mL Pyrex microwave reactor vial. The reactor vial was equipped with a stir bar and sealed using a rubber septum and copper wire to be air-tight. A similar procedure was employed in specific cases where cyanuric acid (CA, 98%), calcium hypochlorite $(Ca(OCl)_2$, technical grade) or ascorbic acid (99%) were used. Hydrochloric acid (HCl) and sulfuric acid $(H_2SO_4)$ employed in specific test reactions were purchased from Fisher Chemicals and Macron chemicals, respectively, and used as received. The aqueous reaction mixture was bubbled with methane gas from a cylinder (Airgas, ultrahigh purity grade) using a steel syringe needle. This procedure was carried out for 20 min under constant stirring and a gas flow rate of 10 $mL.min^{-1}$ to saturate the medium with methane. In methane-free control reactions, the reaction mixture was instead bubbled with Argon gas (Airgas, ultrahigh purity grade) for 30 min under constant stirring and a gas flow rate of 10 $mL.min^{-1}$. Gas saturation was carried out at room temperature. The reactor was then immersed in a water bath at a fixed temperature (25, 30, 35, or 40° C.). For reactions conducted at 0° C. temperature, an ice-water bath was used instead. The reaction was allowed to proceed for 4 hr. It must be noted that trichloroisocyanuric acid is not fully dissolved in the aqueous medium at the start; it gradually dissolves over the course of the reaction.

Characterization of reaction products:

The gaseous products formed in the reaction were analyzed by sampling the headspace of the reactor by gas chromatography (GC) at 1 hr. time intervals. It must be noted that the first sampling, corresponding to a time of 0 h, was performed just prior to placement of the reaction vial in the temperature bath. For GC analysis, 50 µL of the headspace was extracted using a gas-tight Hamilton Luer-lock syringe and injected into a gas chromatograph (GC, Agilent 6850 series) equipped with a flame ionization detector (FID), which has a detection limit of ~50 pg. The peaks in the measured chromatogram were assigned to specific products, primarily chloromethane ($CH_3Cl$), on the basis of chromatograms of standards and verification by mass spectrometry. The chloromethane peak was integrated in ChemStation software. For the quantification of chloromethane, from the peak area measured in the course of a reaction, the peak area measured at time t=0 was subtracted out. The corrected peak area was multiplied by a calibration constant determined separately for chloromethane to yield the molar amount of chloromethane in the injection volume. The actual molar amount of chloromethane in the headspace of the reactor at any time, t, was obtained as follows:

$$\text{Actual molar amount of } CH_3Cl(t) = m_j \left(\frac{v_h}{v_i}\right) + \sum_{i=1}^{j-1} m_i$$

where $m_j$, is the measured molar amount of chloromethane in the injection volume at time t, which also corresponds to the $j^{th}$ injection. $v_h$ and $v_i$ are the reactor headspace volume and injection volume, respectively. The second term in the above equation corrects for the cumulative amount of product removed from the headspace summed over all prior injections. The actual molar amount of $CH_3Cl$ was plotted as a function of time to obtain conversion-time plots. In the case of reactions conducted with calcium hypochlorite and sulfuric acid, there is a rapid generation of chloromethane. Hence, the chloromethane amount at t=0 hr. was also included in the second term above. For every set of reaction conditions, three identical reaction trials were performed, from which the average of the molar amount of chloromethane was determined at time t, which was used to generate the conversion-time plot. The corresponding standard error across the three trials was shown by an error bar for each data-point in the plot.

Mass spectrometric verification of product identity:

For the verification of the identity of the primary product and side products assigned by GC-FID analysis, gas chromatography-mass spectrometry (GC-MS) of the gaseous headspace was obtained from 2 hr. long reactions conducted with a mixture of 20 mg trichloroisocyanuric acid and 3 mL of CH4- or Ar-saturated water in a reactor maintained at 30° C. using a water bath. The analysis of the reaction products was carried out on an Agilent Technologies 7890B gas chromatograph equipped with an Agilent Technologies 5977A mass selective detector. The mass spectrometer was operated in electron-impact ionization mode. A total ion chromatogram (TIC) and mass spectra were measured. The fragmentation pattern, i.e., the intensity as a function of the charge-to-mass ratio (m/z), measured by mass spectrometry was compared with the standard pattern of the putative compound deposited in the National Institute of Standards and Technology (NIST) Chemistry WebBook.

EPR spectroscopy:

An EPR spectrum of a mixture of trichloroisocyanuric acid and water was obtained on a Bruker EMXPlus X-band Continuous Wave EPR instrument using a ER4119HS high sensitivity cavity. The mixture was prepared by stirring 10 mg of trichloroisocyanuric acid with 5 mL of DI water in a 20 mL glass vial for 1 h. During the mixing process, the vial was maintained at a temperature of 30° C. using a water bath. A small amount of the mixture containing the dissolved trichloroisocyanuric acid was then wicked into a thin-walled capillary EPR tube for the spectrum measurement. The measurement was carried out at room temperature using a microwave frequency of 9.84 GHz and signal modulation of 100 KHz.

The spectrum showed a single derivative-absorption line, the g-factor for which was determined using the formula:

$$g = h\nu / \beta B_0$$

where ν is the microwave frequency with a value of 9.84 GHz, h is Planck's constant with a value of 6.626×10-34 J.s, β is the Bohr magneton with a value of 9.274×10-28 J.G-1, and $B_0$ is the magnetic field at the center point of the derivative lineshape (i.e., the location of the maximum slope and therefore the microwave absorption peak maximum) with a value of 3654.24 G. This yielded a g-factor value of 1.92.

Figure 4A:
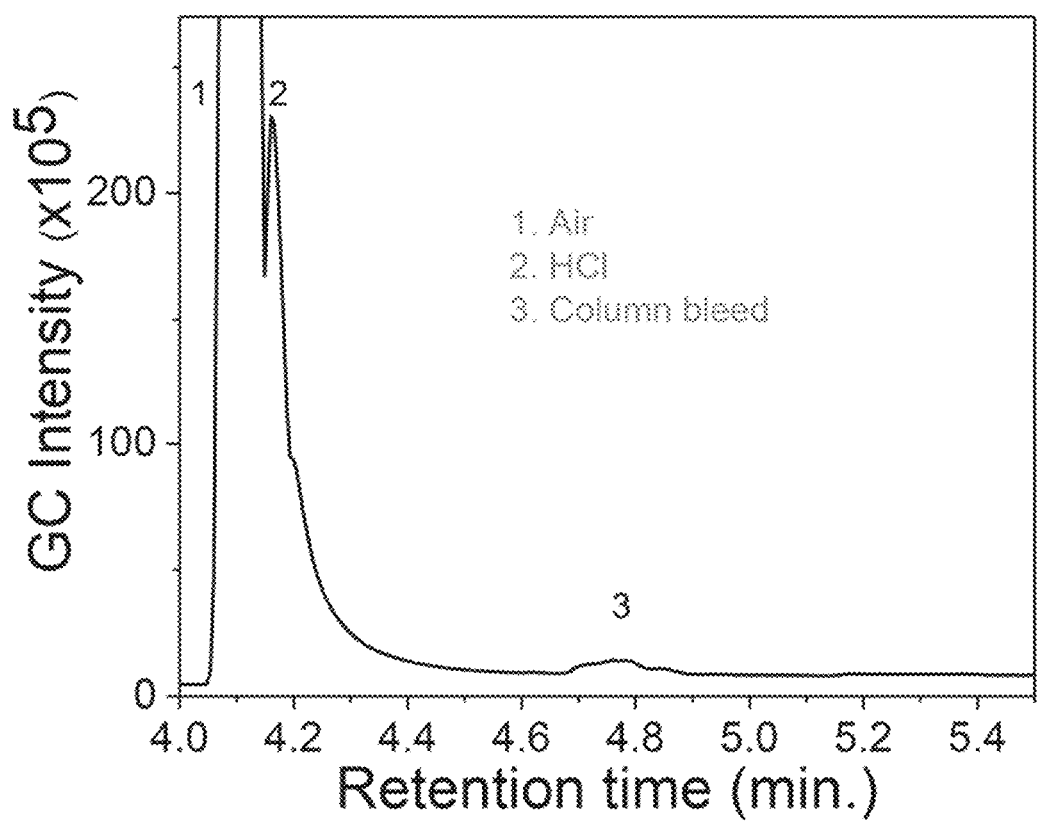
FIG. 4A illustrates the total ion chromatogram measured in the gas chromatography-mass spectrometry characterization of the gaseous headspace of a sealed reactor containing a mixture of trichloroisocyanuric acid and Argon-saturated water maintained at a fixed temperature for 2 hr.
Figure 4B:
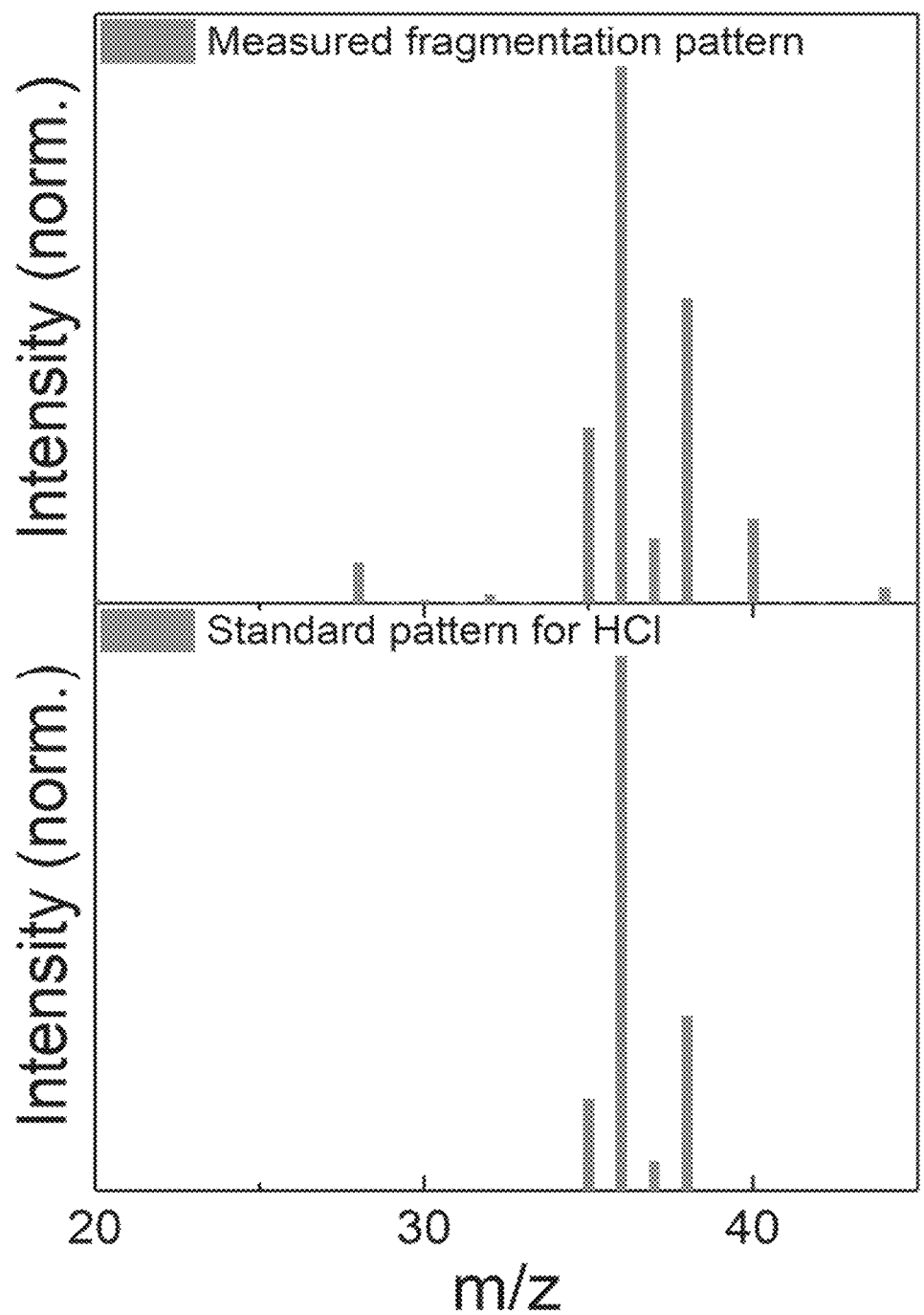
FIG. 4B illustrates the mass spectrum of the hydrochloric acid byproduct of the control reaction conducted with a mixture of trichloroisocyanuric acid and Argon-saturated water.

FIG. 4 illustrates GC-MS characterization of the gaseous headspace obtained from a 2 hr. long reaction conducted with a mixture of 20 mg trichloroisocyanuric acid and 3 mL of Ar-saturated water in a reactor maintained at 30° C. using a water bath. This characterization shows that in the absence of methane, the hypochlorous acid released by the dissolution of trichloroisocyanuric acid in water decomposes to yield HCl. (A) illustrates total-ion chromatogram (TIC) showing a peak (labeled 2), which is assigned to HCl on the basis of the fragmentation pattern shown in B. Contributions, labeled 1 and 3, from air (along with Ar) and column bleed, respectively, were also found. (B) illustrates individual fragmentation patterns for peak 2 measured by mass spectrometry (blue bars) compared with the standard fragmentation pattern for HCl from the NIST Chemistry WebBook (red bars). For the purpose of comparison, in both patterns, the intensity was normalized to its maximum value. The peaks at m/z=28, 32, 40, and 44 in the experimental fragmentation pattern shown here correspond to $N_2$, $O_2$, Ar, and $CO_2$ from air.

Example 1

In this study, reactions were carried out in sealed, gas-tight Pyrex reactor vials (FIGS. 1-5). The reactor contained a mixture of water and trichloroisocyanuric acid pellets, which gradually dissolve into the aqueous medium. The aqueous medium was saturated with methane by bubbling the gas through it. The reactor was immersed in a bath maintained at a fixed temperature (ranging from 0° C. to 40° C.) at which the reaction was allowed to run for 4 hr. Analysis of the gaseous headspace of the reactor by gas chromatography (GC) showed that chloromethane was formed as the primary chlorination product in the reaction (FIG. 1).

FIG. 1 illustrates conversion-time plots for the production of chloromethane in 4 hr. reactions carried out at (A) a fixed amount of 10 mg of trichloroisocyanuric acid and different reaction temperatures, where the inset shows a magnified conversion-time plot for the case of 0° C. and 10 mg of trichloroisocyanuric acid, and (B) at a fixed reaction temperature of 30° C. and different amounts of trichloroisocyanuric acid, where the right-hand-side y-axis of the plot shows the yield of chloromethane determined as a percentage (%) of the initial dissolved molar amount of methane in the reaction mixture. Each reaction was conducted in a sealed glass reactor containing a specific amount of trichloroisocyanuric acid in 3 mL of $CH_4$-saturated water and maintained at a fixed temperature. The gaseous headspace of the reactor was sampled by GC at 1 hr. intervals. Chloromethane was the major product detected. Each data-point is a mean of the molar amount of chloromethane measured across three identical trials; the standard error is shown as the error bar. The reagent conditions in the reactor are dynamic, where trichloroisocyanuric acid dissolves gradually into the aqueous medium over the course of the reaction. In addition, as the reaction progresses, dissolved methane is depleted inducing additional methane from the headspace to dissolve into the aqueous phase. Furthermore, a fraction of the chloromethane produced remains in the aqueous phase and is therefore not quantitatively analyzed by GC.

Figure 1B:
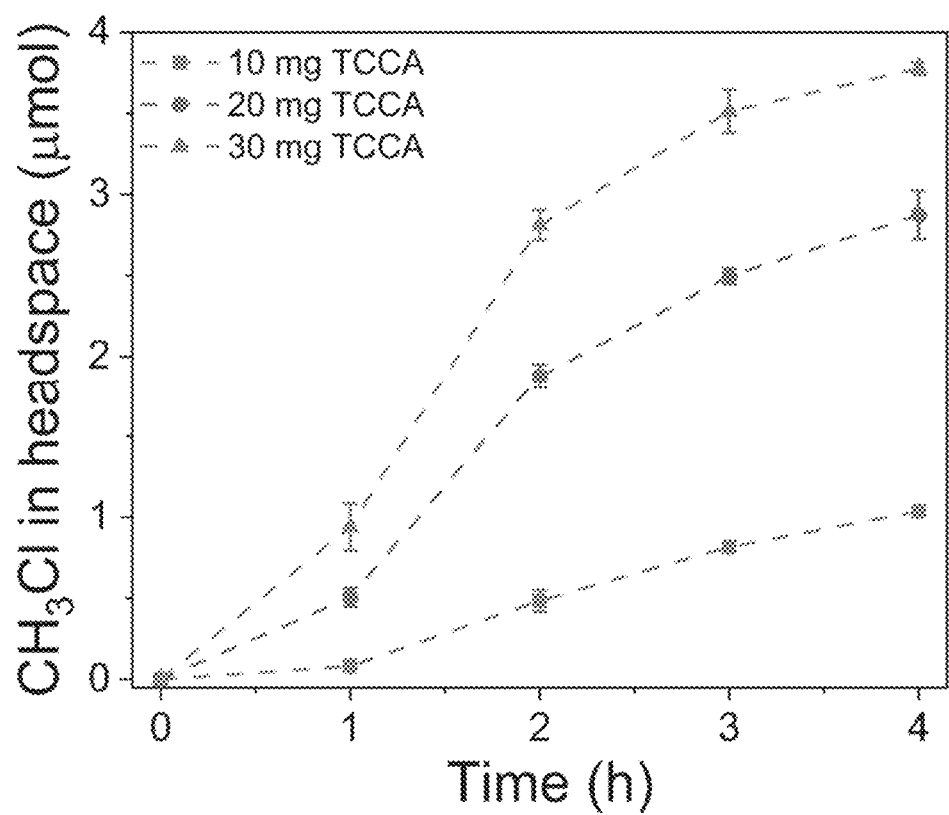
FIG. 1B illustrates conversion-time plots for the production of chloromethane in 4 hr. reactions at a fixed reaction temperature and different amounts of trichloroisocyanuric acid.

The rate and yield of chloromethane production increased with an increase in the reaction temperature at a fixed amount of trichloroisocyanuric acid (FIG. 1A). At 0° C., the rate and yield are three orders-of-magnitude lower than at 30° C., but non-zero (inset of FIG. 1A). The lower reactivity at lower temperatures is likely due not only to sluggish reaction kinetics but also to the reduced solubility of trichloroisocyanuric acid in water. As the temperature increases, there is an increase in the degree of dissolution and dissociation of trichloroisocyanuric acid. In addition, with an increase in the temperature, there is an increase in the rate of dissociation of trichloroisocyanuric acid to form hypochlorous acid and cyanuric acid and also in the rate of the reaction between the hypochlorous acid formed and the dissolved methane.

From the conversion-time plots shown in FIG. 2, there is an uptick in the chlorination rate following 1 hr. of reaction, which suggests that the chlorination reaction is limited by the slow kinetics of dissolution of trichloroisocyanuric acid in water. At the later times, the reaction rate is sustained by the following effect: as the chlorination of methane proceeds and hypochlorous acid is consumed from the aqueous solution, trichloroisocyanuric acid dissolution and dissociation equilibria shift to the right allowing further dissolution of trichloroisocyanuric acid and making hypochlorous acid available for chlorination of methane.

There was also an increase in the rate and yield of chloromethane production with an increase in the amount of trichloroisocyanuric acid at a fixed reaction temperature of 30° C. (FIG. 1B), which can be attributed to the increase in the concentration of dissolved trichloroisocyanuric acid and therefore in that of hypochlorous acid in the aqueous reaction medium. However, this trend tapers off likely due to the solubility limit of trichloroisocyanuric acid in water at 30° C.

There was also an increase in the rate and yield of chloromethane production with an increase in the trichloroisocyanuric acid amount at a fixed reaction temperature (FIG. 1B), which can be explained by the greater availability of hypochlorous acid in the aqueous reaction medium.

Control reactions carried out with Ar-saturated water in the absence of dissolved methane or ethane, 10 mg of trichloroisocyanuric acid, and a reaction temperature of 30° C. gave no detectable products after 4 hr. of reaction. Similarly, control reactions performed at 30° C. with dissolved methane but in the absence of trichloroisocyanuric acid showed no detectable formation of chloromethane. In the latter case, HCl was used to maintain the pH of the reaction mixture at 2.3, close to the acidic conditions prevalent in a mixture of 10 mg of trichloroisocyanuric acid and 3 mL of water, which has a pH of 2.8.

Example 2

Figure 2A:
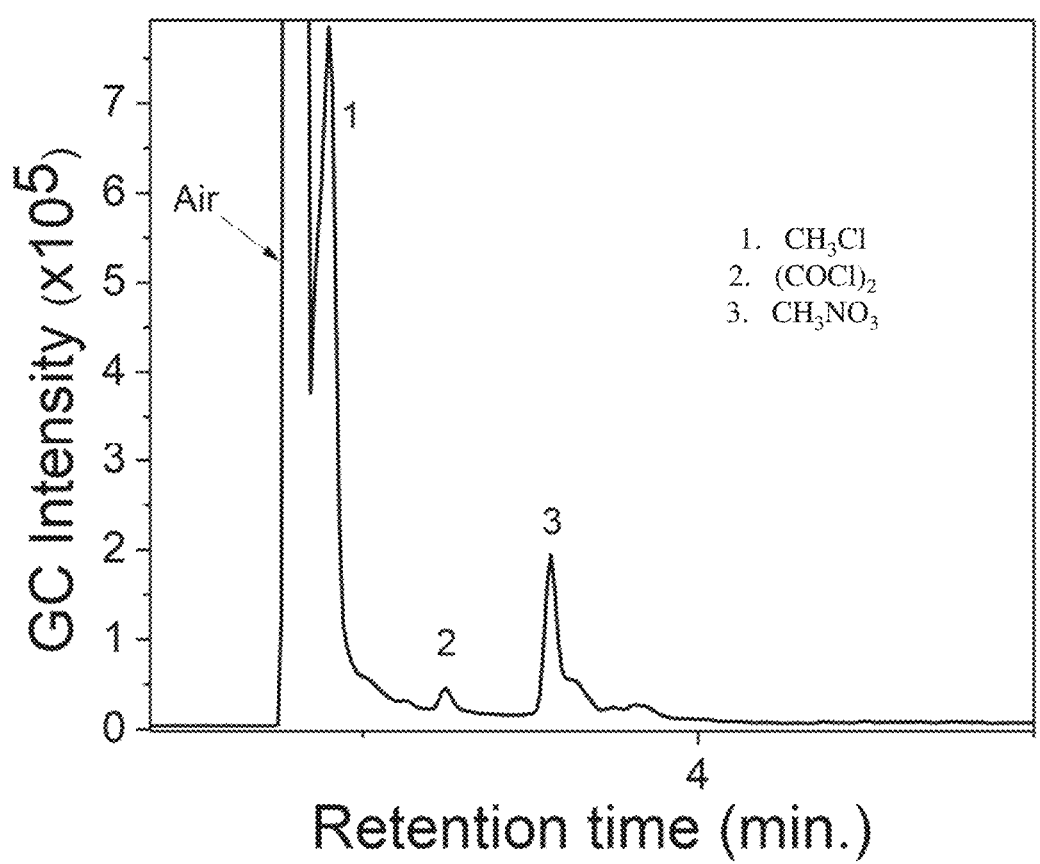
FIG. 2A illustrates a total ion chromatogram measured in the gas chromatography-mass spectrometry characterization of the gaseous headspace of a sealed methane chlorination reactor.
Figure 2B:
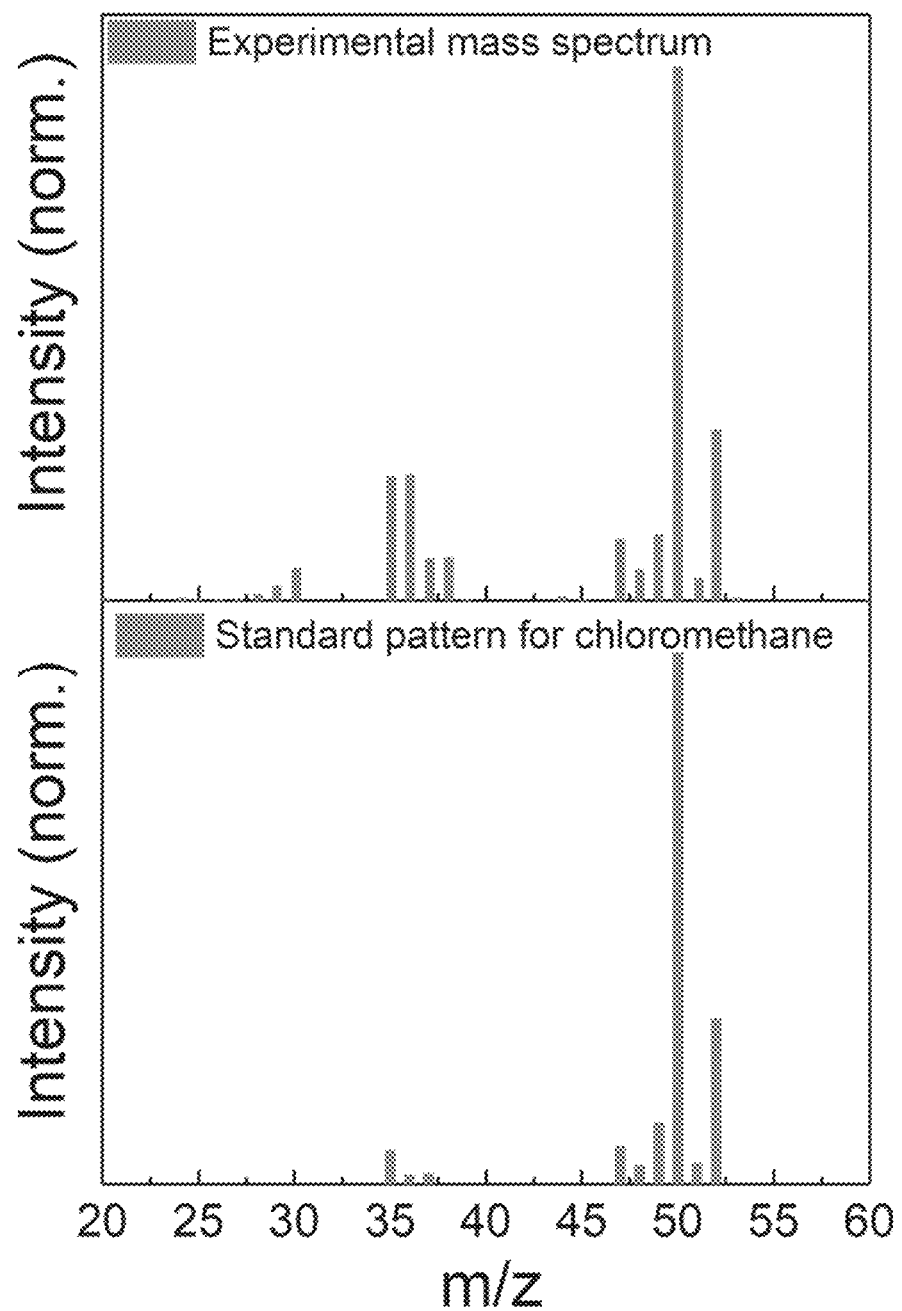
FIG. 2B illustrates the mass spectrum of the chloromethane product of the methane chlorination reaction.
Figure 2C:
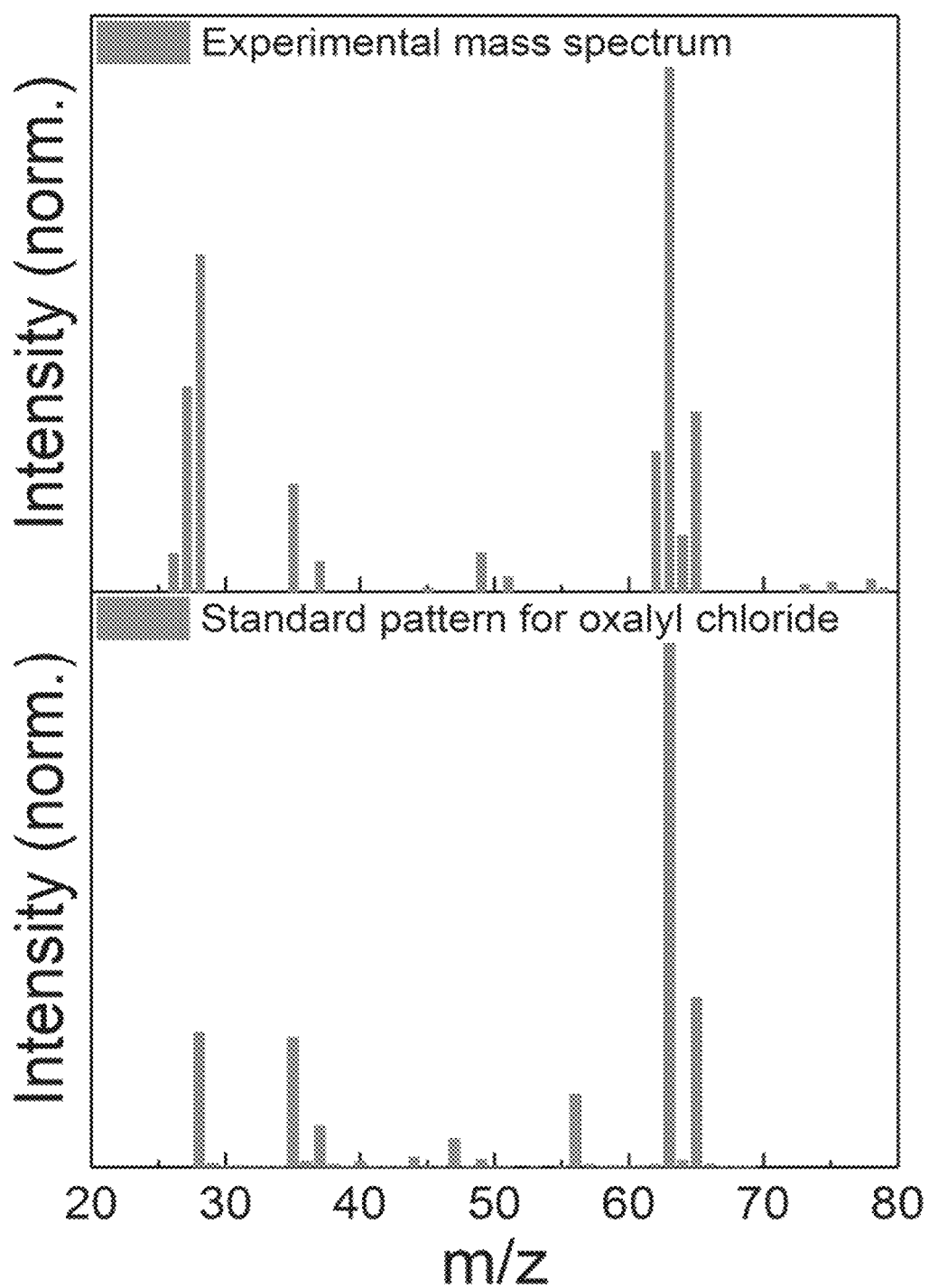
FIG. 2C illustrates the mass spectrum of the oxalyl chloride byproduct of the methane chlorination reaction.
Figure 2D:
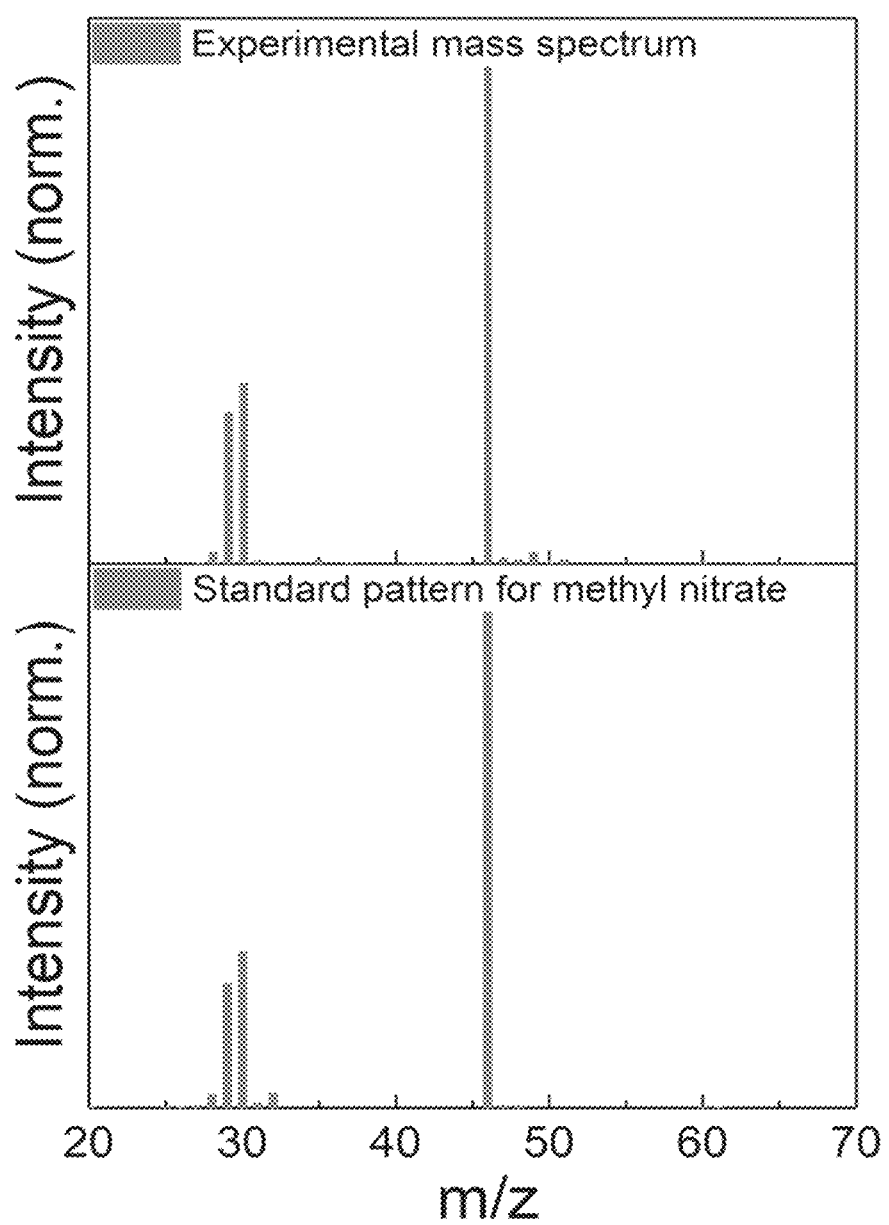
FIG. 2D illustrates the mass spectrum of the methyl nitrate byproduct of the methyl chlorination reaction.

The identity of chloromethane as the major product of the chlorination reaction was confirmed by gas chromatography-mass spectrometry (GC-MS) of the headspace of the reaction mixture after 2 h of reaction at 30° C. (FIG. 2A, B). Methyl nitrate ($CH_3NO_3$) and oxalyl chloride, (($COCl)_2$) were also detected (FIG. 2A, C, D). The latter compounds are likely produced by the decomposition of the organic cyanurate backbone, possibly through the action of the reactive hypochlorous acid species in the aqueous medium. In a control reaction carried out in the absence of dissolved methane, HCl was found from GC-MS to be the major component in the headspace (FIG. 4), which can be attributed to the decomposition of hypochlorous acid to HCl:

$$2HOCl \rightarrow 2HCl + O_2 \qquad (4)$$

FIG. 2 illustrates GC-MS characterization of the products of the methane chlorination reaction. (A) illustrates total ion chromatogram (TIC) of the gaseous headspace of a sealed reactor containing 20 mg of trichloroisocyanuric acid and 3 mL of $CH_4$-saturated water following a 2 hr. reaction at 30° C. Peaks (labeled) in the TIC correspond to the major products generated in the reaction: 1) chloromethane, 2) methyl nitrate, and 3) oxalyl chloride, which were assigned on the basis of the fragmentation patterns observed in electron ionization mass spectra. The peak resulting from the components of air is also shown. (B-D) Individual fragmentation patterns (blue bars) for peaks 1-3, respectively, compared against standard fragmentation patterns (red bars) of chloromethane, methyl nitrate, and oxalyl chloride, respectively, from the National Institute of Standards and Technology (NIST) Chemistry WebBook. For the purpose of comparison, in all measured and standard patterns, the intensity was normalized to its maximum value.

The presence of products other than $CH_3Cl$ is indicated by additional peaks in GC-FID chromatograms, which suggests that the chlorination process probably does proceed beyond monochlorination to form overchlorinated compounds such as di- or trichloromethane. However, overchlorinated compounds are not produced in amounts large enough to be characterized by GC-MS analysis.

Comparative Example 3

Figure 3A:
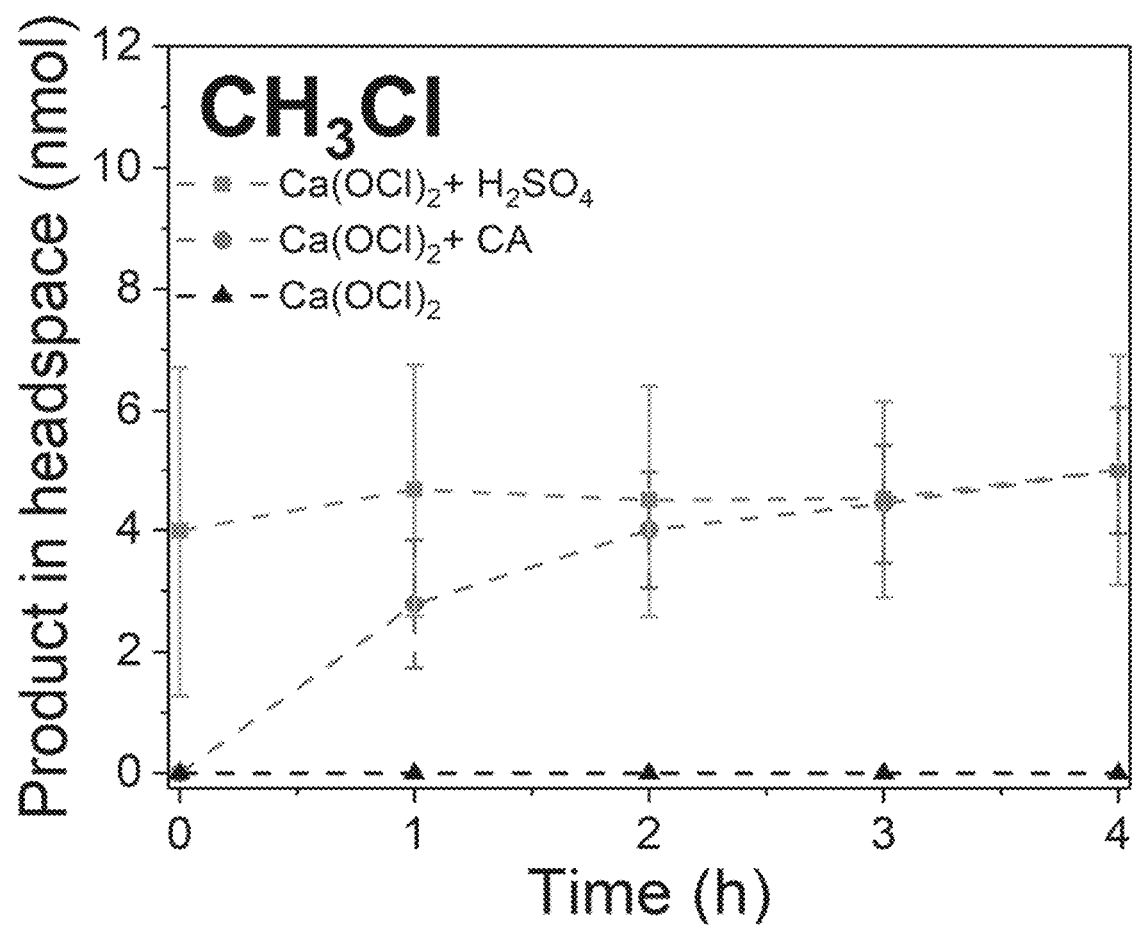
FIG. 3A illustrates conversion-time plots for the production of chloromethane in 4 hr. reactions using an alternate chlorinating agent, calcium hypochlorite.

To gain insight into the mechanism of action of trichloroisocyanuric acid, test reactions were carried out (FIG. 3A) using an alternate chlorinating agent, calcium hypochlorite, which is also a source of hypochlorous acid in water and commonly used in sanitation operations. In reactions conducted with only calcium hypochlorite dissolved in $CH_4$-saturated water, no chloromethane formation was detected. The possible reason for this inactivity is that calcium hypochlorite, which is considerably more soluble in water (0.21 g/mL at 25° C.) than trichloroisocyanuric acid (0.012 g/mL at 25° C.), dissolves and releases hypochlorous acid immediately after mixing. Furthermore, in the basic environment, hypochlorous acid rapidly decomposes making it unavailable for the chlorination of methane that is subsequently bubbled into the aqueous medium. Thus, a source of hypochlorous acid alone may not be sufficient to obtain appreciable conversion. The hypochlorous acid needs to be stabilized against decomposition in the aqueous reaction medium. Cyanuric acid, the organic backbone that remains in water after the release of hypochlorous acid from trichloroisocyanuric acid, is known to be such a stabilizer. When calcium hypochlorite was used along with pre-dissolved cyanuric acid in $CH_4$-saturated water, a small yield of chloromethane was observed (FIG. 3A). This result shows that cyanuric acid stabilizes the hypochlorous acid released by calcium hypochlorite to a degree enough to allow a small extent of methane chlorination. Cyanuric acid reacts with hypochlorous acid to form chlorinated isocyanurates, which serve as a reserve of chlorine. The freely available concentration of highly reactive hypochlorous acid at any given time is limited by the equilibrium between cyanuric acid and chlorinated isocyanurates. The controlled availability of hypochlorous acid is thus favorable for methane chlorination.

The acidity of the aqueous medium containing trichloroisocyanuric acid (the pH for 10 mg of trichloroisocyanuric acid in 3 mL of water is ~2.8) may also play an important role. A high $H^+$ concentration is expected to disfavor hypochlorous acid decomposition to hypochlorite and chlorates. The role of an acidic medium in stabilizing hypochlorous acid was confirmed by a test reaction conducted with calcium hypochlorite and sulfuric acid, which was added to lower the pH of the reaction mixture to ~1.5. Unlike the reaction conducted with only calcium hypochlorite, in the presence of sulfuric acid, methane chlorination was observed (FIG. 3A), albeit with a small yield.

The majority of the conversion appears to take place immediately after reaction components are mixed, which is likely due to the absence of the buffering action of cyanuric acid. Thus, the acidity of the reaction medium and the buffering action of cyanuric acid are two factors responsible for the efficacy of trichloroisocyanuric acid in the chlorination of methane. However, the gradual dissolution of trichloroisocyanuric acid in the aqueous medium appears to be the most important factor; because even in an acidic medium or in the presence of cyanuric acid, the chlorination yield with 20 mg of calcium hypochlorite is three orders-of-magnitude lower than with 20 mg of trichloroisocyanuric acid. The higher solubility of calcium hypochlorite in water results in immediate release of hypochlorous acid. Most of this hypochlorous acid is lost to decomposition before the aqueous medium becomes saturated with dissolved methane.

FIG. 3 illustrates (A) conversion-time plots for the production of chloromethane in 4 hr. reactions conducted in sealed reactors containing 20 mg of calcium hypochlorite, 20 mg of calcium hypochlorite and 20 mg of cyanuric acid, or 20 mg of calcium hypochlorite and 20 µL of 18.4 M $H_2SO_4$ added to achieve a pH~1.5, all with 3 mL of $CH_4$-saturated water. (B) shows conversion-time plots for the production of chloromethane in 4 hr. reactions conducted in sealed reactors containing 10 mg of trichloroisocyanuric acid, 10 mg of trichloroisocyanuric acid and 10 mg of ascorbic acid ($C_6H_8O_8$), or 10 mg of trichloroisocyanuric acid and 50 mg of $C_6H_8O_8$, all with 3 mL of $CH_4$-saturated water. In all cases presented in A) and B), the reactor was maintained at 30° C. and the gaseous headspace was sampled at 1 hr. intervals. Each data-point is a mean of the molar amount of chloromethane measured across three identical trials; the standard error in shown as the error bar. In the reaction conducted with only 20 mg of calcium hypochlorite and the reaction conducted with 10 mg of trichloroisocyanuric acid and 50 mg of $C_6H_8O_8$, chloromethane production, if any, is below the detection limit. The red data-points shown for the reaction with 10 mg of trichloroisocyanuric acid in B correspond to the yellow data-points shown in FIG. 1A. (C) shows a room-temperature EPR spectrum of a mixture of 10 mg of trichloroisocyanuric acid trichloroisocyanuric acid and 5 mL of water prepared at 30° C., showing a single derivative-absorption line with a g-factor of 1.92.

Figure 3B:
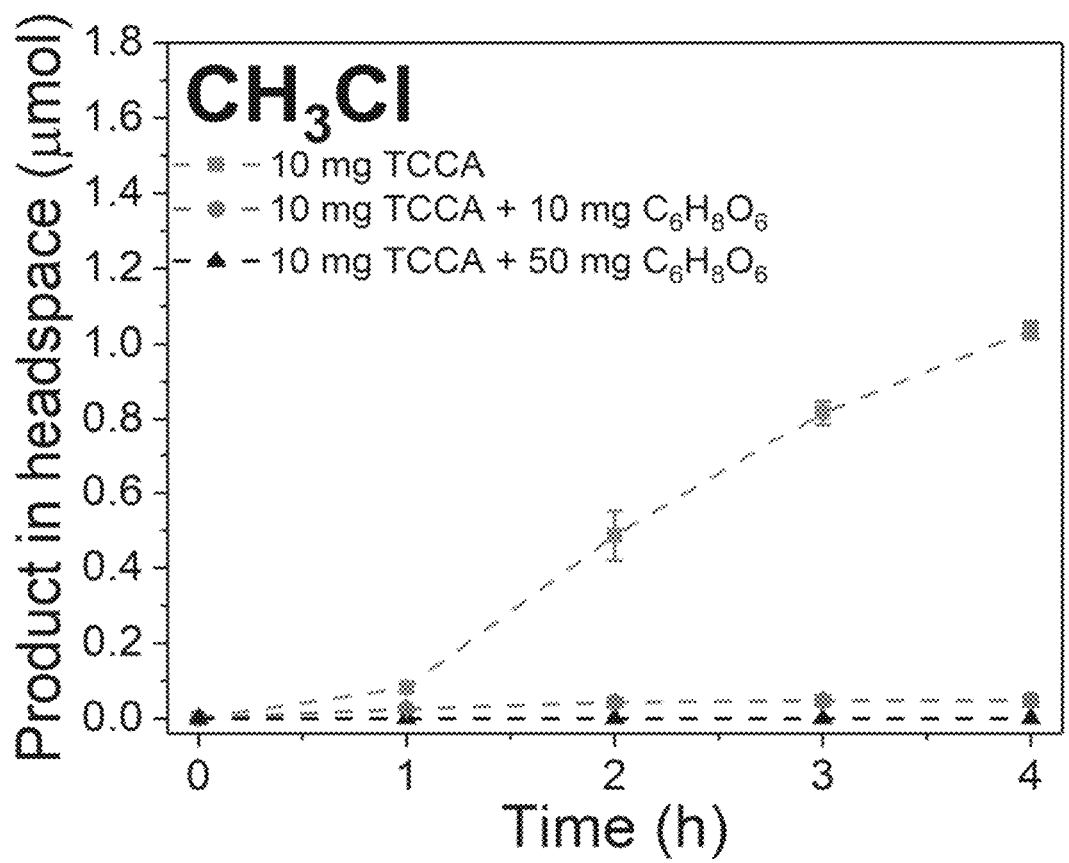
FIG. 3B illustrates conversion-time plots for the production of chloromethane in 4 hr. reactions using trichloroisocyanuric acid and different amounts of ascorbic acid.
Figure 3C:
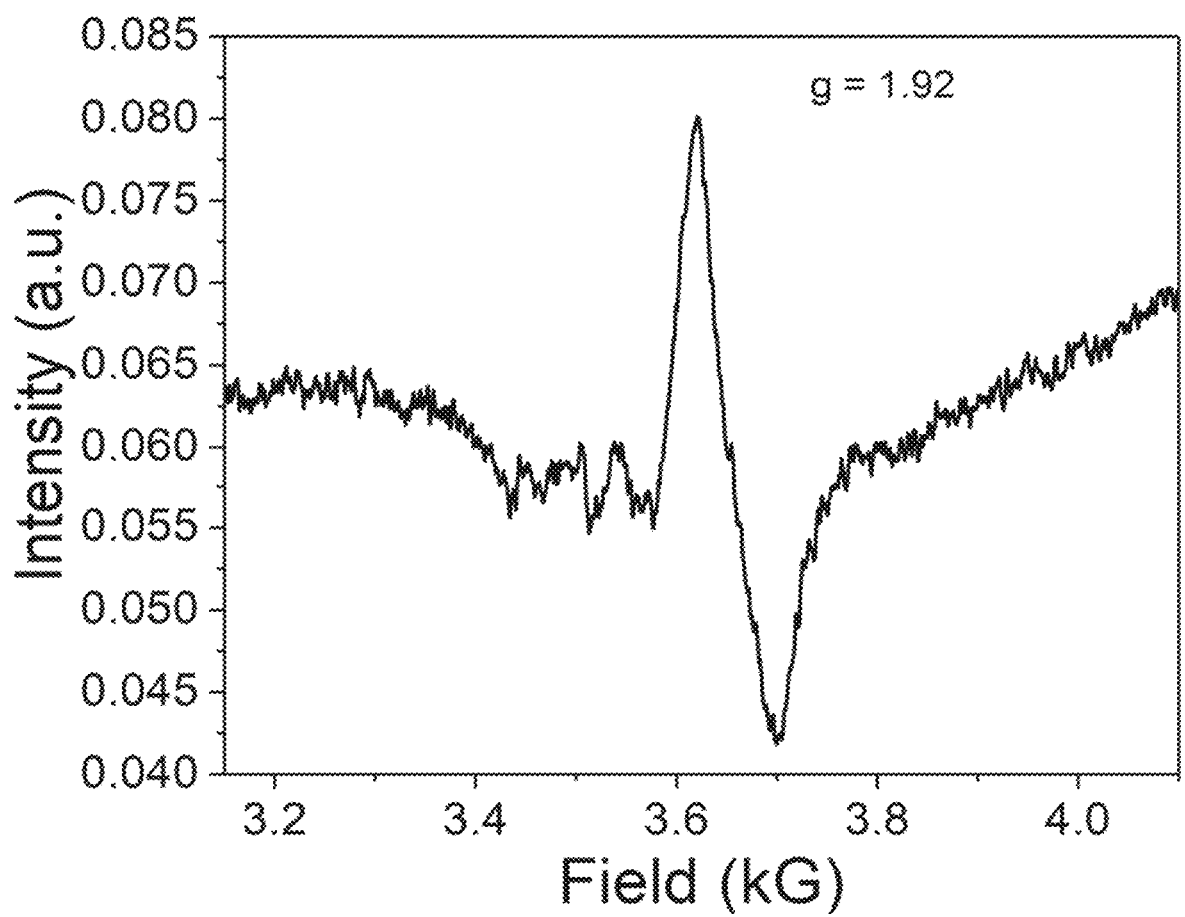
FIG. 3C illustrates an electron paramagnetic resonance (EPR) spectrum that signifies detection of radicals formed in the methane chlorination reaction.

A free-radical mechanism appears to be most plausible for chlorination of methane by hypochlorous acid; hypochlorous acid can dissociate to yield free radicals mediated through a triplet HO'Cl' transition state. To test this hypothesis, a reaction was conducted with ascorbic acid, a free radical scavenger, dissolved in the aqueous medium containing dissolved trichloroisocyanuric acid and methane (FIG. 3B). As compared to the case without ascorbic acid, the presence of 10 mg of dissolved ascorbic acid results in a marked decrease in the yield of methane chlorination. With 50 mg of ascorbic acid, the chlorination reaction is completely suppressed, as evidenced by the lack of detection of any chloromethane. Free radicals, such as HO' and 'Cl, are scavenged by ascorbic acid and therefore unavailable for the abstraction of H' from methane and chlorination to chloromethane. The production of free radicals upon the dissolution of trichloroisocyanuric acid in water is also evidenced by EPR spectroscopy (FIG. 3C). A single derivative-absorption line with a g-factor of 1.92 is observed, which suggests the presence of paramagnetic species with high spin-orbit coupling. Furthermore, the involvement of $'CH_3$ radicals is suggested by the formation of small amounts of ethylene ($C_2H_4$) and acetylene ($C_2H_2$) in the reaction, likely as byproducts of oxidative coupling of two $'CH_3$ radicals.

Example 4

Figure 5:
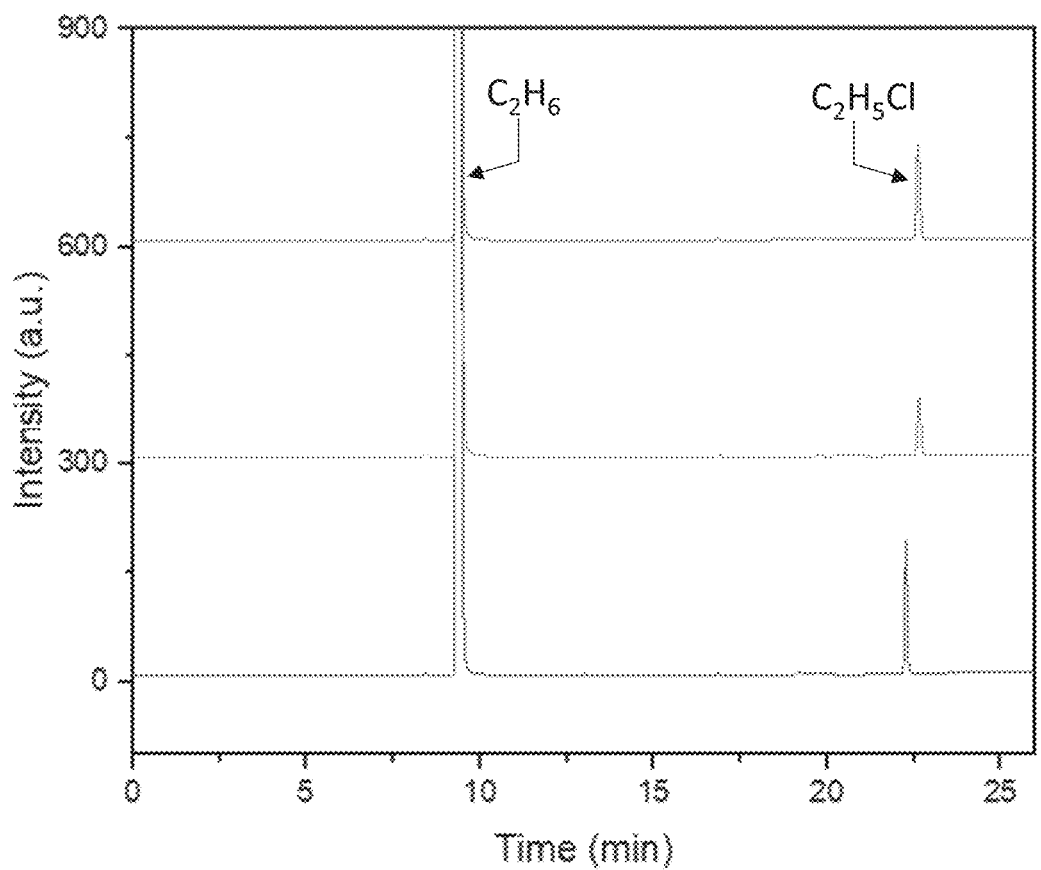
FIG. 5 illustrates gas chromatography-flame ionization detector chromatograms from three identical trials (vertically stacked) of an ethane chlorination reaction.

A series of experiments were conducted to test the chlorination of ethane. The ethane chlorination reactions followed a procedure similar to that of the methane chlorination reactions. In each case, the headspace gas was sampled for GC-FID analysis at the end of a 4 hr. long reaction conducted with a mixture of 10 mg of trichloroisocyanuric acid and 3 mL of $C_2H_6$-saturated water in a sealed reactor, maintained at 30° C. using a temperature bath. Briefly, 10 mg of trichloroisocyanuric acid pellets were mixed with 3 mL of DI water contained in a 10 mL Pyrex reactor vial. The reactor vial was equipped with a stir bar and sealed using a rubber septum and copper wire. The aqueous reaction mixture in the Pyrex reaction vial was saturated with $C_2H_6$ by bubbling ethane from a gas cylinder (Matheson, 99.99%) using a steel needle for 20 min under constant stirring at a gas flow rate of 10 mL.min$^{-1}$. FIG. 5 shows (A) GC-FID chromatograms from three identical trials (vertically stacked) of an ethane ($C_2H_6$) chlorination reaction showing peaks (labeled) at retention times of ~9.5 min and ~22.5 min, corresponding to the reactant, $C_2H_6$, and the monochlorinated product, chloroethane ($C_2H_5Cl$), respectively. No other products were detected.

Other features, advantages and embodiments of the invention disclosed herein will be readily apparent to those exercising ordinary skill after reading the foregoing disclosure. In this regard, while specific embodiments of the invention have been described in considerable detail, variations and modifications of these embodiments can be effected without departing from the spirit and scope of the invention as described and claimed.

We claim:
1. A process for alkane chlorination comprising:
   a. providing an aqueous solution comprising dissolved alkanes selected from methane, ethane or combinations thereof;
   b. providing an 0.005 to 0.050 M aqueous solution of trichloroisocyanuric acid, wherein the trichloroisocyanuric acid in solution forms cyanuric acid and hypochlorous acid; and
   c. contacting the aqueous solution comprising dissolved alkanes with the aqueous solution of trichloroisocyanuric acid, wherein a liquid phase reaction between the dissolved alkanes and the hypochlorous acid forms a gaseous product stream comprising at least one of chloromethane and chloroethane.

2. The process of claim 1, wherein the reaction to form the gaseous product stream is conducted at a temperature of 0° C. to 96° C.

3. The process of claim 2 wherein the temperature is 0° C. to 40° C.

4. The process of claim 3 wherein the temperature is 20° C. to 40° C.

5. The process of claim 1, wherein the gaseous product stream comprises methane.

6. The process of claim 5 further comprising storing the gaseous product stream.

7. The process of claim 6 further comprising treating the stored gaseous product stream to separate chloromethane from other components of the gaseous product stream.

8. The process of claim 1, wherein the liquid phase reaction to form the gaseous product stream is conducted at a pH of 2.0 to 3.5.

9. The process of claim 8 wherein the pH is 2.5 to 3.0.

10. The process of claim 1, wherein the aqueous solution comprising dissolved alkanes is produced by contacting a gas stream comprising at least one of methane and ethane with water to form a saturated alkane solution.

11. The process of claim 1 wherein the aqueous solution is 0.01 M to 0.04 M in trichloroisocyanuric acid.

12. The process of claim 1, wherein the alkane is sourced from a chemical plant, refinery, wastewater treatment plant, landfill, aerobic digester or anaerobic digester.

13. A process for the production of chloromethane or chloroethane comprising:
  a. providing an aqueous solution comprising dissolved alkanes selected from methane, ethane or combinations thereof;
  b. providing a mixture of water and solid trichloroisocyanuric acid, wherein the solid trichloroisocyanuric acid dissolves in water to form cyanuric acid and hypochlorous acid; and
  c. contacting the aqueous solution containing dissolved alkanes with the aqueous solution containing trichloroisocyanuric acid, wherein a liquid phase reaction between the dissolved alkanes and the hypochlorous acid forms a gaseous product stream comprising at least one of chloromethane and chloroethane.

14. The process of claim 13, wherein the solid trichloroisocyanuric acid is in the form of a sphere or a pellet having a diameter of 1.0 mm to 5.0 mm.

15. The process of claim 13, wherein the reaction to form the gaseous product stream is conducted at a temperature of 0° C. to 96° C.

16. The process of claim 13, wherein the gaseous product stream comprises methane.

17. The process of claim 13, wherein the liquid phase reaction to form the gaseous product stream is conducted at a pH of 2.0 to 3.5.

18. The process of claim 13, wherein the aqueous solution comprising dissolved alkanes is produced by contacting a gas stream comprising at least one of methane and ethane with water to form a saturated alkane solution.

19. The process of claim 13, wherein the alkane is sourced from a chemical plant, refinery, wastewater treatment plant, landfill, aerobic digester or anaerobic digester.

20. A process for the production of chloromethane or chloroethane comprising:
  a. providing an aqueous solution comprising dissolved alkanes selected from methane, ethane or combinations thereof; and
  b. adding solid trichloroisocyanuric acid to the aqueous solution comprising dissolved alkanes, wherein the solid trichloroisocyanuric acid dissolves to form cyanuric acid and hypochlorous acid, and a liquid phase reaction between the dissolved alkanes and hypochlorous acid forms a gaseous product stream comprising at least one of chloromethane and chloroethane.

21. The process of claim 20, wherein the reaction to form the gaseous product stream is conducted at a temperature of 0° C. to 96° C.

22. The process of claim 20, wherein the gaseous product stream comprises methane.

23. The process of claim 3, wherein the liquid phase reaction to form the gaseous product stream is conducted at a pH of 2.0 to 3.5.

24. The process of claim 3, wherein the solid trichloroisocyanuric acid is in the form of a pellet having a diameter of 1.0 mm to 5.0 mm.

25. The process of claim 20, wherein the aqueous solution comprising dissolved alkanes is produced by contacting a gas stream comprising at least one of methane and ethane with water to form a saturated alkane solution.

26. The process of claim 20, wherein the alkane is sourced from a chemical plant, refinery, wastewater treatment plant, landfill, aerobic digester or anaerobic digester.

27. A process comprising:
  a. adding an aqueous solution comprising dissolved alkanes selected from methane, ethane or combinations thereof to a reactor comprising a liquid phase stream and a bulk gas phase stream above the liquid phase; and
  b. adding solid trichloroisocyanuric acid to the aqueous solution comprising dissolved alkanes, wherein the solid trichloroisocyanuric acid dissolves to form cyanuric acid and hypochlorous acid, and a liquid phase reaction between the dissolved alkanes and hypochlorous acid forms a gaseous product stream comprising a chlorinated alkane product comprising at least one of chloromethane and chloroethane that moves to the bulk gas phase stream of the reactor, wherein the bulk gas phase stream comprises the chlorinated alkane products and at least one of methane and ethane.

28. The process of claim 27 further comprising transferring the bulk gas phase stream to a storage facility.

29. The process of claim 28 further comprising transferring the bulk gas phase stream from the storage facility to a treatment facility where the chlorinated alkane products is separated from other components in the bulk gas phase stream.

* * * * *